(12) United States Patent
Kuzelka

(10) Patent No.: US 8,781,558 B2
(45) Date of Patent: Jul. 15, 2014

(54) SYSTEM AND METHOD OF RADIATION DOSE TARGETING THROUGH VENTILATORY CONTROLLED ANATOMICAL POSITIONING

(75) Inventor: Russell James Kuzelka, Madison, WI (US)

(73) Assignee: General Electric Company, Schenectady, NY (US)

( * ) Notice: Subject to any disclaimer, the term of this patent is extended or adjusted under 35 U.S.C. 154(b) by 37 days.

(21) Appl. No.: 13/290,468

(22) Filed: Nov. 7, 2011

(65) Prior Publication Data

US 2013/0116555 A1    May 9, 2013

(51) Int. Cl.
| | |
|---|---|
| *A61B 5/00* | (2006.01) |
| *A61N 5/00* | (2006.01) |
| *A61B 6/03* | (2006.01) |
| *A61M 16/00* | (2006.01) |

(52) U.S. Cl.
CPC ... *A61B 6/03* (2013.01); *A61N 5/00* (2013.01); *A61M 16/00* (2013.01)
USPC .............. 600/427; 600/534; 600/428; 607/42

(58) Field of Classification Search
USPC .............................. 600/427, 428, 534; 607/42
See application file for complete search history.

(56) References Cited

U.S. PATENT DOCUMENTS

| | | | |
|---|---|---|---|
| 5,067,494 A | | 11/1991 | Rienmeuller et al. |
| 6,078,639 A | * | 6/2000 | Heuscher ........................ 378/15 |
| 6,148,814 A | * | 11/2000 | Clemmer et al. ........ 128/200.24 |
| 6,597,939 B1 | * | 7/2003 | Lampotang et al. .......... 600/427 |
| 7,393,329 B1 | | 7/2008 | Wong et al. |
| 2008/0039713 A1 | * | 2/2008 | Thomson et al. ............. 600/411 |

OTHER PUBLICATIONS

Suh, Y., Aperture maneuver with compelled breath (AMC) for moving tumors: A feasibility study with a moving phantom, Med. Phys. 31 (4), 760-766 (Apr. 2004).*

* cited by examiner

*Primary Examiner* — Rajeev Siripurapu

(57) ABSTRACT

The system and method of the present application includes an image guided radiation therapy (IGRT) system, combined with a medical ventilator, to form a closed-loop system to optimize treatment of a tumor for patients who cannot comply with a normal respiratory management procedure. The ventilator may be used to generate respiratory maneuvers to facilitate clean images for dose planning, so that clinicians can more clearly visualize a target with fewer of the image artifacts associated with respiratory motion. The combined IGRT and ventilation systems approach facilitates treatment of specific organs most susceptible to respiratory motion artifact, and helps minimize the doses to the heart in left-breast treatments. Improved positioning of the anatomical target structures for exposure to external beam radiation may be accomplished through combinations of respiratory-gating, respiratory pause, and selective right or left lung mechanical ventilator techniques.

7 Claims, 4 Drawing Sheets

SYSTEM AND METHOD OF RADIATION DOSE TARGETING THROUGH VENTILATORY CONTROLLED ANATOMICAL POSITIONING

FIELD

The present application is directed to the field of radiation oncology and intraoperative radiation therapy. More specifically, the present application is directed to the field of radiation dose targeting through ventilator control.

BACKGROUND

The motion of the respiratory cycle affects tumor sites in the thoracic cavity, abdomen and pelvis. The relative position of target carcinomas of the breast and lung in the thoracic compartment, liver, stomach and pancreas in the abdominal compartment, and prostatic and gynecologic carcinomas within the pelvic compartment are all affected by respiration. Intrafraction target motion, (tumor motion occurring within a treatment session) is an issue that is becoming increasingly important with external beam radiotherapy. Intrafraction motion can be caused by one, or a combination of, the respiratory, musculoskeletal, cardiac, and gastrointestinal systems, with the respiratory system being the dominant cause of tumor motion during treatment. The ultimate goal for dose delivery is to obtain a static target relative to the treatment beam's eye view whenever the beam is on and deliver radiation only to the tumor, sparing the surrounding healthy tissue. Effective dose targeting is becoming increasingly important, as dose-escalation is used in an attempt to improve long-term tumor control and improve patient survival.

Respiratory motion, the most significant contributor to intrafraction motion, can generate artifacts in all imaging modalities. Patient's breathing patterns can vary in magnitude, period and regulation during imaging and treatment sessions. If respiratory motion is not considered during image acquisition, when conventional radiotherapy techniques are used, artifacts are created in the acquired image and can distort the target volume and provide the clinician with incorrect positional and volumetric information of the tumor. For example, with computed tomography (CT) imaging, the artifacts primarily occur because different parts of 3D target structure(s) move in and out of a 2D slice window during the respiratory cycle and time of acquisition.

During radiation treatment planning, margins are allocated to ensure adequate coverage of the tumor and surrounding area for suspected microscopic spread of cancerous cells. Additional treatment margins are also added to accommodate tumor intrafraction and interfraction motion (motion between treatment sessions), as well as patient setup error. Adding treatment margins to cover the limits of tumor motion due to respiration is non-optimal because this increases the radiation field size and thus exposes a volume of healthy tissue to high doses of radiation which can create additional complications.

In an attempt to mitigate respiratory induced intrafraction tumor motion, techniques called "Deep Inspiration Breath Hold" (DIBH) and "Active Breathing Control" (ABC) have been developed. In the DIBH technique, the patient is verbally coached and brought to a reproducible deep inspiration breath-hold level. Active Breathing Control has been used and found to be fairly effective in stabilizing lung volume, and in the case of patients with lung tumors, lung tumor position. In this approach, a spontaneously breathing patient breathes through a valve that is closed depending on a respiratory signal derived from a digital spirometer and held closed while the radiation beam is turned on. However, the ABC and DIBH techniques are only applicable and useful for those patients who are alert, oriented, cooperative and understand the respective coaching instructions required of both methods. The breath-hold method is typically difficult for lung cancer patients, for which respiratory motion management is most critical, as they cannot hold their breath for extended periods due to compromised pulmonary function.

SUMMARY

The system and method of the present application includes an image guided radiation therapy (IGRT) system, combined with a medical ventilator, to form a closed-loop system to optimize visualization, positioning, and treatment of a tumor for those patients whom cannot comply with a normal respiratory management procedure; i.e., DIBH or ABC. The combined external beam radiation therapy and ventilation systems approach facilitates treatment of specific organs most susceptible to respiratory motion artifact, including the lungs, liver, stomach and pancreas, and may help minimize the dose delivered to the heart in left-sided breast cancer treatments. This may be accomplished by improved anatomical positioning of target structures through a combination of ventilator controlled automated respiratory-gating, respiratory pause, and selective right or left lung ventilation. By having direct volume, phase and duration control of the patient's respiratory cycle, the ventilator may be used to 1) generate respiratory maneuvers to facilitate clean images for dose planning, so that clinicians can more clearly visualize a target with fewer of the image artifacts associated with respiratory motion, and 2) optimize the physical position of the target for actual dose delivery.

In one aspect of the present application, a radiation dose targeting system comprises a ventilator configured to provide ventilation to a patient, an image guided radiation therapy (IGRT) unit in two-way communication with the ventilator and configured to treat a target structure in the patient, and a controller, wherein the controller coordinates the operation of the ventilator and the IGRT to focus treatment on the target structure.

In another aspect of the present application, a method of radiation dose targeting comprises imaging a target area of a patient with an image guided radiation therapy (IGRT) unit, wherein the target area includes a target structure, adjusting the position of the target structure and internal organs of the patient with the ventilator, such that the adjusting step optimizes the position of the target structure for treatment, and treating the patient by irradiating the target structure with the IGRT.

In another aspect of the present application, a radiation dose targeting unit comprises a ventilator component configured to provide ventilation to a patient, an external beam radiation unit and an imaging device, wherein the external beam radiation unit and the imaging device are in two-way communication with the ventilator, and the external beam radiation unit is configured to treat a target structure in the patient, and a controller, wherein the controller coordinates the operation of the ventilator, the imaging device and the external beam radiation unit to focus treatment on the target structure.

DETAILED DESCRIPTION

In the present description, certain terms have been used for brevity, clearness and understanding. No unnecessary limitations are to be applied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. §112, sixth paragraph, only if the terms "means for" or "step for" are explicitly recited in the respective limitation.

Currently, most treatment rooms used in the art do not have respiratory motion management devices, and treatment planning has to consider methodologies to accommodate respiratory motion. Based on a respiration-correlated CT (RCCT), a common clinical approach is to estimate the gross tumor volume (GTV) in each phase of the CT scan and determine treatment planning based on the combination of each of the individual scans to points in the respiratory cycle. However, variations of breathing from cycle to cycle and potential changes in tumor position from day to day are complicating factors.

Respiratory-gating is a treatment technique which allows the treatment beam to turn on and off at specific points within the respiratory cycle. In the current state of the art in respiratory-gated treatment planning, the duty cycle for the treatment is typically planned to be 30% to 50%. The duty cycle is determined by the ratio of gate duration to the respiratory period.

During delivery of the dose, the actual duty cycle can vary from that originally planned due to the variability of the patient's breathing. Controlled ventilation may be able to increase the duty cycle, increasing delivered dose, and reducing overall treatment time.

Figure 1:
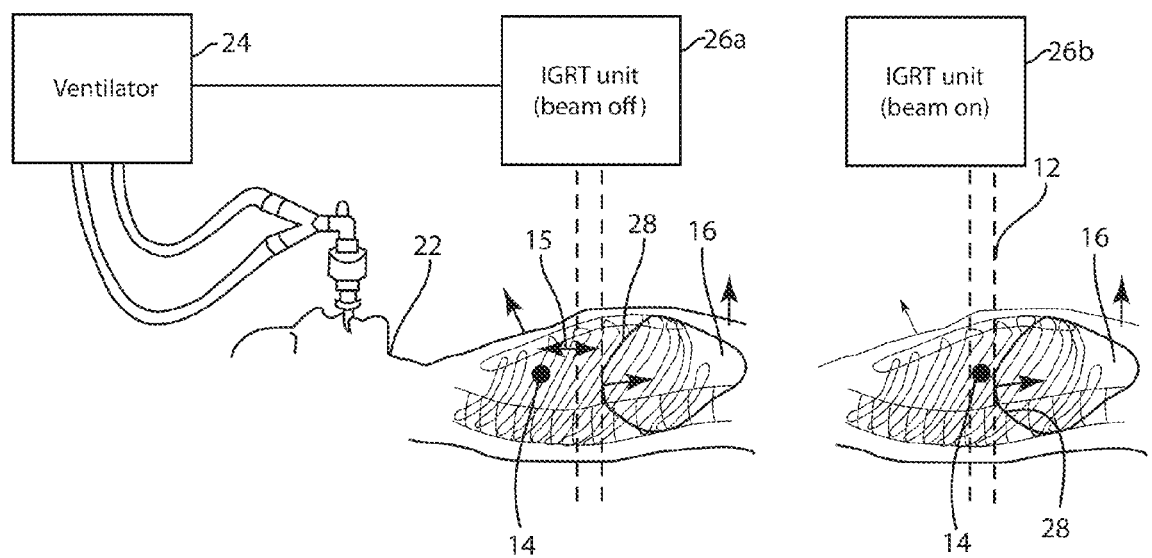
FIG. 1 is a block diagram illustrating an embodiment of the system of the present application.
Figure 2:
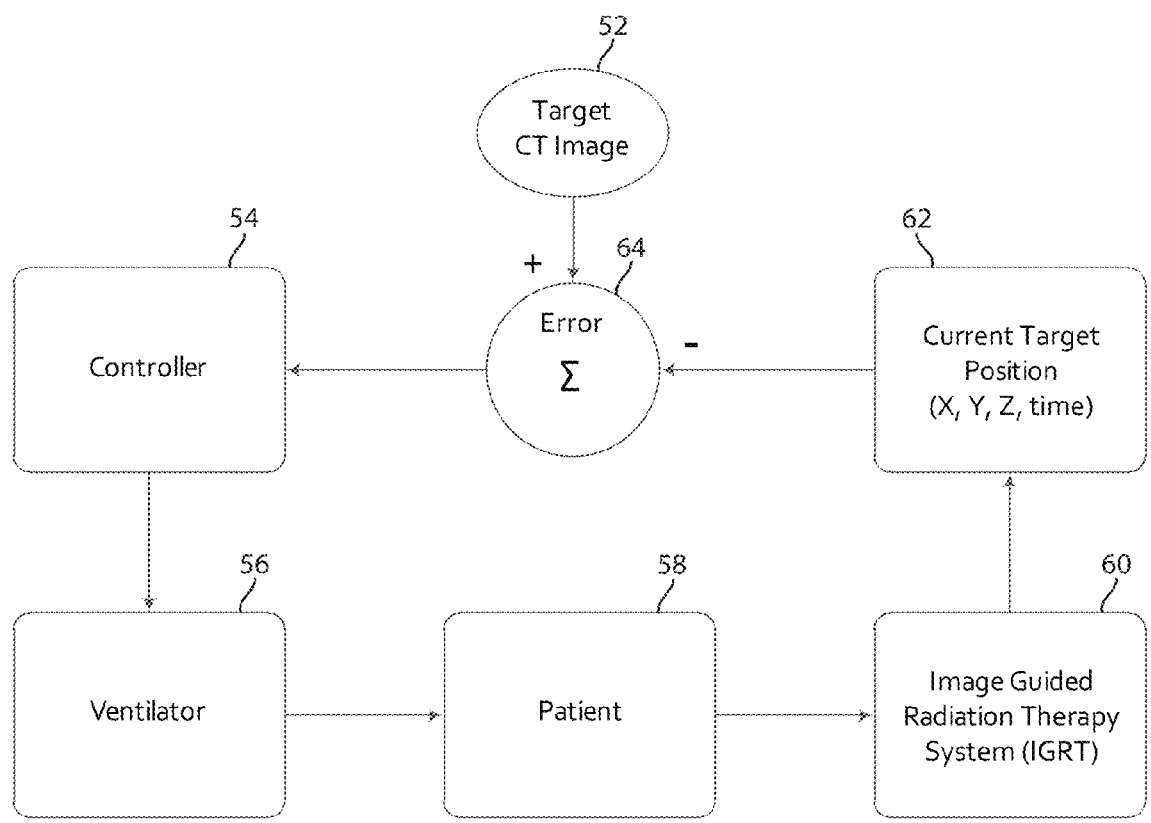
FIG. 2 is a flow chart illustrating an embodiment of the system of the present application.

For thoracic and abdominal tumors, the exhalation phases of the respiratory cycle (deep exhale) are commonly used for the treatment because patients typically spend more time in exhalation than inhalation and the exhalation phase is typically more reproducible than inhalation. However, gating at inhalation has the advantage that critical anatomical structures are further from the treatment field. As an example, during inhalation, the heart moves inferiorly and posteriorly and therefore, gated left-breast treatments during inhalation can reduce the cardiac dose; sparing cardiac tissue from an unintended dose. Also, during deep inhalation, the lung is expanded to a greater degree which means that the fraction of lung irradiated for a given beam aperture is smaller during inhalation than for other phases of the respiratory cycle Referring to FIG. 1, a block diagram of a system of the present application illustrates movement of a target structure 14 due to internal organ 16 movement from patient breathing along a tumor path 15. The patient 22, and the movement of the internal organs 16 of the patient 22 results in the movement of the target structure 14 along the tumor path 15 into and back out of a treatment field 12. FIG. 2 illustrates a ventilator 24, an external beam radiation delivery unit (i.e, IGRT unit) 26a and 26b, and further illustrates the diaphragm 28 of the patient 22 moving the internal organs and chest cavity of the patient during breathing. It should be noted that the system 20 of the present application may include an external beam radiation delivery unit (i.e., IGRT unit) 26 in communication with a separate ventilator 24. However, it is also contemplated that the ventilator 24 and IGRT 26 may include a combined unit for ease of application. It should further be noted that the IGRT unit 26 and ventilator 24 are shown in block form, but are understood to be fully functional components that treat and/or monitor the patient in the specific ways that they are designed. The IGRT 26a illustrates an IGRT with the treatment beam off, while 26b illustrates the same IGRT with the treatment beam on, as will be described in greater detail below.

Utilizing the system 20 of FIG. 2 for a ventilator controlled breath, the lung and diaphragm 28 can be recruited for full inflation (i.e., deep inhale) and held in time and space for the required treatment by the ventilator 24. This may have the added benefit of reducing the amount of healthy, critical tissue (cardiac and lung) from unnecessary exposure to the treatment field 12. Likewise, direct control of the patient 22 breath would more precisely allow synchronization of inspiratory and expiratory phases of the anatomy to that of the irradiation.

The system and method of the present application includes at least two, embodiments including system 20 having a dynamic method, wherein the IGRT unit 26 images target motion at controlled ventilator 24 settings in real time, and optimizes/plans motion tracking, as necessary, to deliver the required dose, and a static embodiment, wherein the IGRT unit 26 initiates a breath-hold (apneic period) when the target structure 14 has been identified and anatomically optimized for treatment.

The IGRT unit 26 can command the ventilator 24 to ventilate the lung(s) of the patient to learn the specific required volume/pressure to achieve the best image and exposure of the thoracic/abdominal/pelvic target structure 14 of interest. This training time would allow the IGRT 26 system to fine tune exposure of target structure 14 in the planning stages of therapy.

As a non-limiting example, in a dynamic method, multiple breaths may be delivered to the patient 22 to determine repeatability between images and predict target trajectory; taking into account the compliance and settling time of the lung(s). Information on settling time can be provided by measured data from the ventilator 24, and an optimal time at which to trigger treatment can be determined by the host IGRT 26. Algorithm(s) in the IGRT 26 host modality control and fine tune target 14 motion and positioning via the ventilator 24, to produce the best opportunity for radiation delivery using acquired images as feedback. It should be noted that following the description above, there is bi-directional communication functionality between the ventilator 24 and the IGRT 26.

Referring now to FIG. 2, a closed-loop system 50 of the present application as described above is illustrated in block diagram. Here, a target CT image 52 is coordinated at a lung volume defined during a planning stage and a controller 54 having a storage medium and a processor operates the ventilator 56 that is ventilating the patient 58. It should be noted that the controller 54 may be implemented in the ventilator 56, the IGRT 60, in both of these two elements, or in a separate standalone computer (not shown). The IGRT unit 60 treats the patient 58 as described above and outputs a current target position 62 that includes three-dimensional position data of the patient and the target structure 52, as well as a set of time data that reflects the optimal position of the target structure 52. This current target position data 62 is used to make an error adjustment 64 that is imputed back to the controller 54 for further ventilator 56 and IGRT unit 60 operation. In short; real-time adjustments are made to the ventilator 56 as required by the controller to optimize and/or hold the position of the target for optimal beam therapy.

Figure 3:
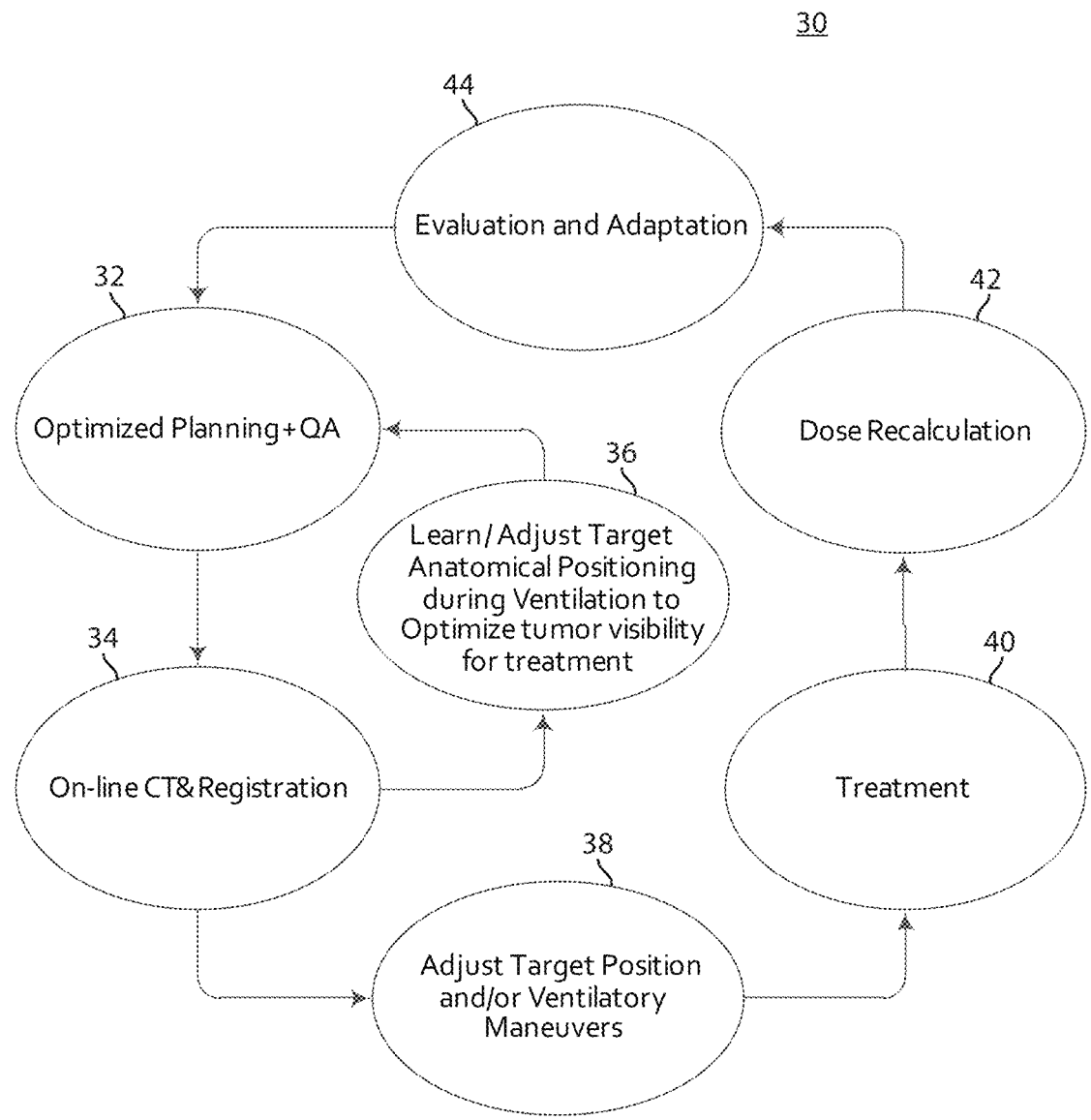
FIG. 3 is a block diagram illustrating an embodiment of the system of the present application.

Referring now to FIG. 3, a method 30 of radiation dose targeting is illustrated in the flow chart. In step 44, the patient is evaluated and a planning step 32 is implemented in order to prepare the patient. In step 34, an image of the target area is taken. In step 36, the method 30 responds by adjusting the target structure positioning during ventilation to optimize the tumor visibility for treatment. Steps 32-36 are repeated until the target position is optimized for tumor visibility and treatment. Then, in step 38, the target position is adjusted and/or ventilatory maneuvers are made in order to treat the patient in step 40. The dose of the treatment is recalculated in step 42, and the method is repeated as needed starting with step 44, taking into account the treatment and dose recalculation from steps 40 and 42.

Deep-inspiration breath hold (DIBH) is a reproducible state of maximum breath-hold and is advantageous for treating thoracic tumors, because it significantly reduces respiratory tumor motion and related internal anatomy changes such that if often protects critical normal tissues. Though predominantly applied to lung cancer radiotherapy, breath-hold methods also are valuable in breast cancer radiotherapy. Though the intrafraction motion is small for normal free-breathing respiration, during inhalation the diaphragm pulls the heart posteriorly and inferiorly away from the breast, and therefore there is potential for reducing both cardiac and lung dose. Because DIBH is relatively demanding for patients, it is typically only used for adult, compliant patients in whom the significant lung inflation allows treatment to a higher total dose than would be possible with free breathing.

Static Breath Control by Ventilator (SBCV) as described above is a proposed method to facilitate reproducible breath-hold during thoracic radiotherapy for those patients incapable of performing the maneuver.

The goal of SBCV is to allow the ventilator 24 to suspend breathing at any predetermined volume and position within the mechanical respiratory cycle to reduce thoracic tumor motion during radiotherapy. The most common and likely clinical position for breath hold being moderate or deep inhale breath-hold (mDIBH/DIBH) near 100% capacity. The anesthesia ventilator 24 contains an air flow sensor, which may be a differential pressure transducer or hot wire anemometer, which measures gas flow to and from the patient 22, while the controller 54 integrates the flow sensor signal to obtain the volume of gas delivered during the breath cycle, which is then displayed and recorded as a function of time.

The intended value of DIBH required to achieve the optimum internal organ displacement, or anatomical positioning of the target structure 14, would typically be calculated after a fully exhaled baseline. Because the system 20 will be delivering mechanical breaths, the value of each breath should be consistent and repeatable. Typically, the ventilator 24 can deliver from to 0 to 70 cmH20 of ventilation pressure in a healthy adult and provide the clinician wide control of degree of lung inflation during breath-hold events.

Figure 4:
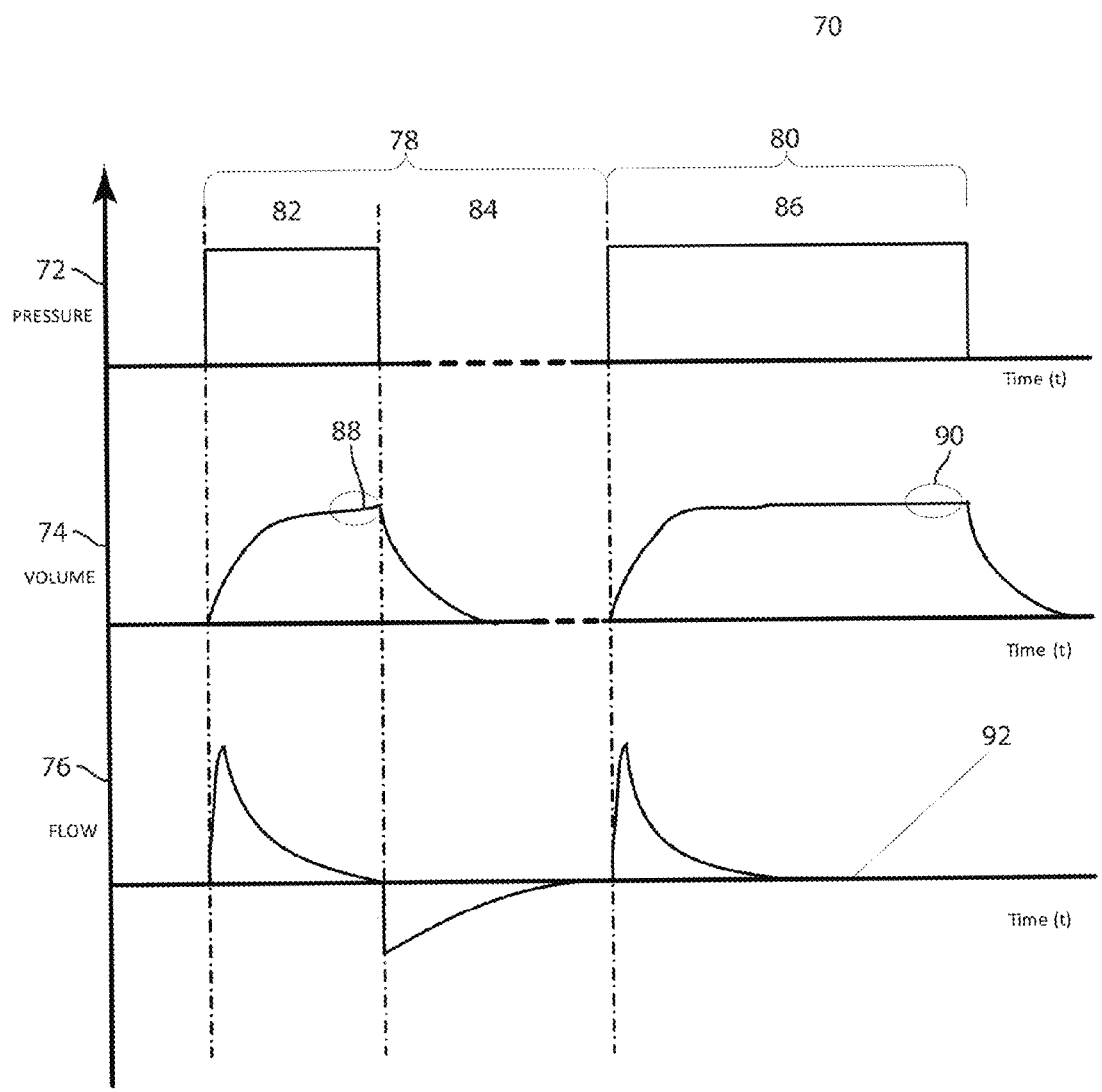
FIG. 4 is a graphical representation of patient waveforms according to an embodiment of the present application.

Referring to FIG. 4, a set of waveforms 70 is illustrated showing a mechanical breath pressure waveform 72, a volume waveform 74 and a flow waveform 76, illustrating a learning phase 78 and a treatment phase 80 according to the present application. It should be noted that reference to other figures may be made during the description of these waveforms 70. Prior to radiotherapy treatment, the ventilator 24 will first perform a learning phase. The learning phase may involve delivery of multiple mechanical breaths to the patient 22, with the intent of producing a slow vital capacity maneuver, consisting of a deep inspiration 82 until plateau, deep exhalation until plateau 84, and then a second deep inspiration or DIBH at which time the required breath-hold would be initiated in a treatment phase 80.

Pressure control such as this supplies a constant set pressure during inspiration as shown by the plateaus. The ventilator 24 calculates the inspiratory time from the frequency and I:E ratio settings. A high initial flow pressurizes the circuit to the set inspiratory pressure. The flow then decreases to maintain the set pressure (Pinspired). Pressure sensors in the ventilator 24 measure patient airway pressure. The ventilator 24 automatically adjusts the flow to maintain the set inspiratory pressure. It should be noted that the volume waveform 74 includes an indication of the maximum volume 88 and a point in the treatment phase 80 when this maximum volume allows for the enablement of therapy 90. It should also be noted that during this treatment, the flow waveform 76 shows zero flow 92.

While the ventilator 24 is providing a mechanical breath, as determined in the ventilator 24 learning phase 78 above, real-time fluoroscopic, x-ray or CT images would be obtained with the goal of capturing at least one complete vital capacity breath cycle from inspiration 82 to expiration 84, and would be time correlated to the breath delivered by the mechanical ventilator 24. The controller 54 may then determine at what phase (in time) the breath should be held and the dose delivered in relation to the time stamp of the planning fluoroscopy, cine or CT images. In consultation with the images obtained during the planning phase, the clinician may decide at what percent capacity or at what phase/volume of the breath cycle the lungs should be maintained to optimize target structure 14 exposure during radiotherapy. These values would then be programmed into the controller 54.

The controller may then initiate the therapy with a start command to the ventilator 24. The ventilator 24 then begins executing the breath maneuver defined in the therapy learning phase 78 in order to reach the required lung capacity while simultaneously transmitting real-time ventilator data to the controller 54. Once the controller 54 has determined that the specified target volume has been reached, breath hold would be initiated, the treatment beam turned on, and the therapeutic dose delivered to the target structure 14. Once the treatment has been completed, the ventilator 24 would return to normal mechanical ventilation.

Although the breath hold duration is envisioned to be defined by the controller 54, as discussed above, the ventilator 24, equipped with an appropriate controller 54, may have capability to provide feedback on the physiological status of the patient 22 during radiotherapy. In the instance that any physiological patient 22 parameters exceed allowable limits pre-defined by the ventilator 24, the ventilator 24 automatically restores mechanical ventilation of the patient 22 to ensure appropriate oxygenation.

The ventilator 24 communicates this data to the controller 54 which performs an analysis and quality test on the ventilator 24 data to determine if the breaths are sufficiently repeatable in both volume and duration for use in treatment. The controller 54 compares volumes at deep exhale and second deep inhale with user-set thresholds. After confidence has been established in repeatability and reproducibility of the ventilator and patient configuration, the therapy learning phase 78 may commence.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A radiation dose targeting system, comprising a controller, a ventilator configured to provide a plurality of mechanical respiratory cycles to a patient, an imaging system configured to capture images of a target structure in the patient throughout at least one of the mechanical respiratory cycles provided by the ventilator, an image guided radiation therapy (IGRT) unit, wherein the ventilator and IGRT are configured to bi-directionally communicate during a planning stage and a treatment stage in order to treat the target structure in the patient, wherein: during the planning stage, using acquired images from the imaging system as feedback, algorithms in the IGRT are configured to determine an optimal position of the target structure via the ventilator such that the target structure is within a radiation treatment field of the IGRT field and such that a lung volume provided by the ventilator reduces the amount of healthy tissue from unnecessary exposure to the radiation treatment field, and the IGRT is configured to output a set of time data which correlates to a phase in time of at least one mechanical respiratory cycle that reflects an optimal position of the target structure, and during the treatment stage, the ventilator is configured to initiate a mechanical respiratory cycle to reach the phase in time that reflects the optimal position of the target structure, the controller is configured to initiate breath hold when the optimal position of the target structure is reached, the IGRT is configured to treat the target structure during the breath hold, the IGRT is further configured to output three-dimensional position data of the target-structure during the breath hold and three-dimensional position data of the patient during the breath hold to the controller, and the controller is further configured to make real-time error adjustments to the ventilator based on the three-dimensional position data outputted from the IGRT in order to maintain the optimal position of the target structure.

2. The system of claim 1, wherein the IGRT includes an external beam radiation unit.

3. The system of claim 1, wherein the ventilator and the IGRT are housed in a single physical unit.

4. The system of claim 1, wherein the ventilator is programmed with allowable limits of physiological patient parameters, the ventilator configured to communicate the allowable limits to the controller.

5. The system of claim 4, wherein the controller is configured to provide feedback on a physiological status of the patient during the radiotherapy treatment.

6. The system of claim 1, wherein the controller is located in the IGRT.

7. The system of claim 1, wherein the controller is located in the ventilator.

* * * * *